United States Patent [19]
Petzoldt et al.

[11] Patent Number: 4,894,336
[45] Date of Patent: Jan. 16, 1990

[54] RACEMIC DISSOCIATION OF 3-ACYLOXY BICYCLO(3.3.0)OCTAN-7-ONE-2-CARBOXYLIC ACID ESTERS BY STEREOSPECIFIC ENZYMATIC OR MICROBIOLOGICAL ACYLATE HYDROLYSIS

[75] Inventors: Karl Petzoldt; Helmut Dahl; Werner Skuballa, all of Berlin, Fed. Rep. of Germany

[73] Assignee: Schering Aktiengesellschaft, Berlin and Bergkamen, Fed. Rep. of Germany

[21] Appl. No.: 237,109

[22] PCT Filed: Nov. 12, 1987

[86] PCT No.: PCT/DE87/00513
§ 371 Date: Jul. 13, 1988
§ 102(e) Date: Jul. 13, 1988

[87] PCT Pub. No.: WO88/03567
PCT Pub. Date: May 19, 1988

[30] Foreign Application Priority Data
Nov. 13, 1986 [DE] Fed. Rep. of Germany ....... 3638758

[51] Int. Cl.$^4$ .................. C12P 41/00; C12P 17/02; C12P 7/42; C07C 177/00
[52] U.S. Cl. .................... 435/146; 435/155; 435/156; 435/197; 435/280; 435/252.1; 560/116; 560/117; 560/119; 549/336
[58] Field of Search ............. 435/146, 155, 156, 280, 435/197; 560/116, 117, 119, 501

[56] References Cited
U.S. PATENT DOCUMENTS

| | | | |
|---|---|---|---|
| 4,644,068 | 2/1987 | Shibasaki et al. | 549/214 |
| 4,762,936 | 8/1988 | Shibasaki et al. | 560/117 |
| 4,774,341 | 9/1988 | Shibasaki et al. | 562/501 |
| 4,814,468 | 3/1989 | Mori et al. | 549/336 |

FOREIGN PATENT DOCUMENTS
2582648 12/1986 France.

OTHER PUBLICATIONS
Tetrahedron vol. 42 #1 1986 Mori et al., pp. 435-444.
Chem. Pharm Bull. vol. 33 No. 7 1985 K. Kojima et al., pp. 2688-2696.

*Primary Examiner*—Herbert J. Lilling
*Attorney, Agent, or Firm*—Millen, White & Zelano

[57] ABSTRACT

Process for the production of optically active (+)-bicyclo[3.3.0]octanol derivatives of formula (+)-I, in which $R_1$ and $R_2$ represent jointly an oxygen atom or the double-bond residue —O—X—O— with X as a straight or branched-chain alkylene with 1-7 C-atoms, or $R_1$ and $R_2$ represent separately the residue $OR_5$ with $R_5$ as a straight or branched-chain alkyl with 1-7 C-atoms, and $R_3$ the residue COOZ with Z as a hydrogen atom, straight or branched chain alkyl with 1-7 C atoms, cycloalkyl with 3-6 C atoms, phenyl or aralkyl with 7-10 atoms or $R_3$ is the residue —$(CH_2)_n$—O—$COR_4$ with n having the meaning 1-4 and $R_4$ as a straight or branched-chain alkyl with 1-7 C atoms, cycloalkyl with 3-6 C atoms, phenyl or aralkyl with 7-10 C atoms. The process is characterized in that racemic 3α-cyloxy-cis-bicyclo[3.3.0]-octane derivatives of formula (+)-II, wherein $R_1$, $R_2R_3$ and $R_4$ have the above meanings, are subjected enzymatically or microbiologically to a stereospecific acylate hydrolsis and the (+)-bicyclo[3.3.0]-octanol derivative produced is separated from the unsaponified bicyclo[3.3.0]-octanol acylate of formula (−)-II or the unsaponified enantiomers (+)-II are separated from the saponified bicyclo[3.3.0]octanol derivative (−)-I and then subjected to chemical acylate hydrolysis.

10 Claims, No Drawings

RACEMIC DISSOCIATION OF 3-ACYLOXY BICYCLO(3.3.0)OCTAN-7-ONE-2-CARBOXYLIC ACID ESTERS BY STEREOSPECIFIC ENZYMATIC OR MICROBIOLOGICAL ACYLATE HYDROLYSIS

The invention relates to a process for stereospecific acylate hydrolysis of racemic 3-acyloxy-bicyclo[3.3.0]octan-7-one-2-carboxylic acid esters to optically active 3-alcohols with the help of enzymes or microorganisms.

It is particularly suitable for the production of optically active (+)-bicyclo[3.3.0]octanol derivatives of formula (+)-I.

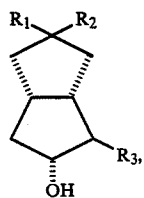

in which $R_1$ and $R_2$ together mean an oxygen atom or a double-bond radical —O—X—O— with X as straight-chain or branched-chain alkylene with 1–7 C atoms or $R_1$ and $R_2$ mean in each case the radical $OR_5$ with $R_5$ as straight-chain or branched-chain alkyl with 1–7 C atoms and $R_3$ means the radical COOZ with Z as hydrogen atom, straight-chain or branched-chain alkyl with 1–7 C atoms, cycloalkyl with 3–6 C atoms, phenyl or aralkyl with 7–10 C atoms or $R_3$ means the radical -(CH$_2$)n-O-COR$_4$ with n meaning 1–4 and $R_4$ as straight-chain or branched-chain alkyl with 1–7 C atoms, cycloalkyl with 3–6 C atoms, phenyl or aralkyl with 7–10 C atoms.

It is characterized in that racemic 3alpha-acyloxy-cis-bicyclo[3.3.0]octane derivatives of the formula (±)-II

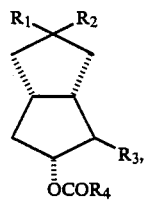

in which $R_1$, $R_2$, $R_3$ and $R_4$ have the above-indicated meanings, are enzymatically or microbiologically subjected to a stereospecific acylate hydrolysis and the resulting (+)-bicyclo[3.3.0]octanol derivative (+)-I is separated from the unsaponified bicyclo[3.3.0]octanol acylate of formula (−)-II or the unsaponified enantiomer (+)-II is separated from the saponified bicyclo[3.3.0]octanol derivative (−)-I and then subjected to a chemical acylate hydrolysis.

If X means a straight-chain or branched-chain alkylene radical with 1–7 C atoms, the following radicals are meant by it: —CH$_2$)n with n=1–7 (methylene, ethylene, tri-, tetra-, penta-, hexa— and hepta—methylene, —C(CH$_3$)$_2$—, —CH(CH$_3$)—, —CH((CH$_3$)—CH$_2$—, —C(CH$_3$)$_2$—CH$_2$—, —CH$_2$—CH(CH$_3$)—, CH$_2$—C(CH$_3$)$_2$, —CH$_2$—CH(CM$_3$)—CH$_2$—, —CH$_2$—C(CH$_3$)$_2$—CH$_2$—, —CH—(C$_2$H$_5$)—, —C(C$_2$H$_5$.)$_2$—, —CH(C$_2$H$_5$)—CH$_2$—, —C(C$_2$H$_5$)$_2$—CH$_2$—, —CH$_2$—CH(C$_2$H$_5$)—, —CH$_2$—C(C$_2$H$_5$)$_2$—, —CH$_2$—CH(C$_2$H$_5$)—CH$_2$—, —CH$_2$—C(C$_2$H$_5$)$_2$—CH$_2$— etc Z, $R_4$ and $R_5$ as straight-chain or branched-chain alkyl radicals with 1=7 C atoms mean methyl, ethyl, n-propyl, isopropyl, n-butyl, isobutyl, sec-butyl, tert-butyl, n-pentyl, isopentyl, sec-pentyl, neopentyl, n-hexyl, isohexyl, n-heptyl, isoheptyl.

Z or $R_4$ as aralkyl radicals with 7–10 C atoms are to comprise the following radicals:

—CH$_2$—C$_6$H$_5$, —CH$_2$—CH$_2$—C$_6$H$_5$, —CH$_2$—CH$_2$—CH$_2$—C$_6$H$_5$,

—CH$_2$—CH$_2$—CH$_2$—CH$_2$—C$_6$H$_5$, —CH—C$_6$H$_5$,
                                                    |
                                                   CH$_3$

—CH$_2$—CH—C$_6$H$_5$, —CH$_2$—CH$_2$—CH—C$_6$H$_5$,
         |                              |
        CH$_3$                          CH$_3$

—CH—CH$_2$—C$_6$H$_5$, —CH—CH$_2$—CH$_2$—C$_6$H$_5$,
  |                       |
 CH$_3$                   CH$_3$

—CH$_2$—CH—CH$_2$—C$_6$H$_5$, —CH—C$_6$H$_5$,
         |                       |
        CH$_3$                  C$_2$H$_5$

—CH$_2$—CH—C$_6$H$_5$, —CH—C$_6$H$_5$, —C(CH$_3$)$_2$—C$_6$H$_5$,
         |              |
        C$_2$H$_5$     C$_3$H$_7$

—CH$_2$—C(CH$_3$)$_2$—C$_6$H$_5$, —CH—CH—C$_6$H$_5$
                                |    |
                               CH$_3$ CH$_3$

—C(CH$_3$)$_2$—CH$_2$—C$_6$H$_5$ etc.

Z or $R_4$ as cycloalkyl radicals with 3–6 C atoms comprise the following radicals: cyclopropyl, cyclobutyl, cyclopentyl, cyclohexyl.

Optically active 6alpha-carbaprostacyclin and especially some compounds derived from it have, as stable analogs of the natural prostacyclin (PGI$_2$), a high therapeutic benefit [R. C. Nickolson, M. H. Town, H. Vorbrueggen: Prostacyclin Analogs, Medical Research Reviews, Vol. 5, No. 1, pp. 1–53 (1985). The syntheses specified in this more recent survey are long and lead partially only to racemic carbacyclins. The syntheses, which lead to the carbacyclins in the absolute configuration corresponding to the natural PGI$_2$, are especially costly. This is due to the fact that readily accessible, suitable initial materials are achiral and the optical activity must be introduced into the intermediate stages suitable for this purpose only in the course of the synthesis.

Several syntheses already start from optically active 7alpha-hydroxy-6beta-hydroxymethyl-2-oxa-bicyclo[3.3.0]octan-3-one derivatives. Thus the problem of the introduction of optical activity is inde desolved. But further multistage synthesis sequences must still be performed for the substitution of the 2-oxa function by a methylene group, to reach derivatives of 3alpha-hydroxy-2beta-hydroxymethyl-bicyclo[3.3.0]octan-7-one, which are suitable for the attachment of alpha and omega chains typical, respectively, for the carbacyclin analogs.

A more recent publication describes the use of cis-bicyclo[3.3.0]octan-3,7-dione derivatives for synthesis of optically active carbacyclins. Kojima et al. describe in Chem. Pharm. Bull. 33, 2688 (1985) a process, which includes the separation of diastereomeric salts of the racemic 7,7-ethylenedioxy-3alpha-hydroxy-cis-bicyclo[3.3.0]octane-2-carboxylic acid.

This process also still requires 7 reaction steps to reach the starting material for carbacyclin analogs starting from 3-oxoglutaric esters. In addition, an unstable beta keto acid intermediate stage is passed through.

Further, for the production of optically active carbacyclin analogs, as described above, no synthesis method, which allows a simple production, is known.

As enzymes there are suitable for the process according to the invention preferably
lipase-PL from Alcaligenes (Meito Sangyo company)
lipase My from Candida cylindracea (Meito Sangyo company)
lipase "Saiken" from Rhizopus (Nagase company)
lipase "Sclerotinia" (Nagase company)
alpha-chymotrypsin from cattle pancreas (Chemical Dynamics Corporation)
alcalase T (Novo Industrias company)
esterase from hog liver (Boehringer Mannheim)
lipase from hog pancreas (Chemical Dynamics Corporation)
subtilisin from *Bacillus subtilis* (Boehringer Mannheim),
and the enzymes can be used both in dissolved, suspended form or immobilized form e.g. on CNBr-activated sepharose or on oxirane acrylic beads or in any other immobilized form.

As microorganisms there are suitable for the process according to the invention preferably:
*Alcaligenes marshallii* ATCC 21030
*Mucor rouxii* ATCC 8097
*Corynebacterium equi* ATCC 21107
*Trichoderma koningi* CBS 85068
*Sarcina lutea* ATCC 9341
*Penicillium citrinum* ATCC 8506
*Flavobacterium lutescens* IFO 3085
*Alcaligenes paradoxus* ATCC 17713

But the enzymes isolated from microorganisms can also be used in dissolved or immobilized form.

The optically active bicyclooctane derivatives of formula (+)-I, which can be produced by the process according to the invention, represent valuable intermediates for the synthesis of pharmacologically effective prostacyclin derivatives. The plurality of enzymes and microorganisms which can be used for stereospecific hydrolysis saponify the racemic 3alpha-cyloxy-cis-bicyclo[3.3.0]octane derivatives of formula (±)-II to optically active alcohols of formula (+)-I, which in their absolute configuration correspond to the natural prostacyclin PGI$_2$. This results by a comparison of the spectral and optical properties with comparison substances, which can be produced in a standard way from intermediate stages of a synthesis of optically active carbacyclin analogs. The products thus obtained, after separation of the unsaponified "false" enantiomer (-)-II, can be used directly for synthesis of analogs corresponding to the natural prostacyclin PGI$_2$.

But there are also microorganisms and enzymes such as, e.g., alpha-chymotrypsin or alcalase T., which saponify the "false" unnaturally configured enantiomer of the two components of racemate (±)-II to (-)-I. In this case the remaining unsaponified enantiomer (+)-II is used for synthesis of PGI$_2$ analogous carbacyclins.

The process according to the invention works otherwise according to generally known process conditions, which are usually used in enzymatic reactions or microbiological conversions and can be seen from the examples. The course of the enzymatic or microbiological conversion is followed by analysis of continuously taken samples. Suitable as analysis methods are HPLC or thin-layer chromatographic quick analyses (silica gel plates of the Merck/Darmstadt company, development by means of ether, staining by means of sulfuric acid/ethanol).

The reaction is discontinued and the batch is worked up, when 50% of racemic substrate used is converted.

The enzymatic or microbiological stereospecific acylate saponification according to the invention is suitable especially for acylate saponification of the following racemic prostacyclin intermediate stages:

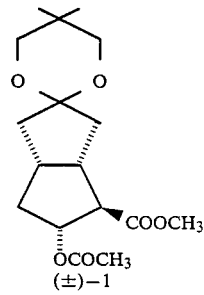

OCOCH$_3$
(±)-1

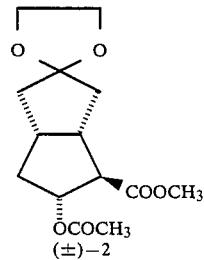

OCOCH$_3$
(±)-2

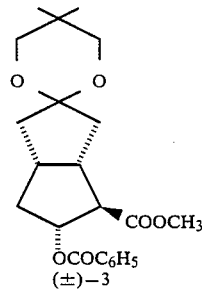

OCOC$_6$H$_5$
(±)-3

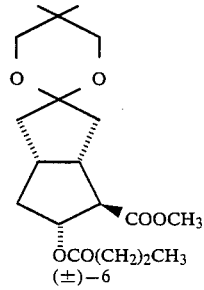

OCO(CH$_2$)$_2$CH$_3$
(±)-6

-continued

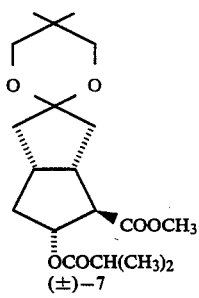

COOCH₃
OCOCH(CH₃)₂
(±)-7

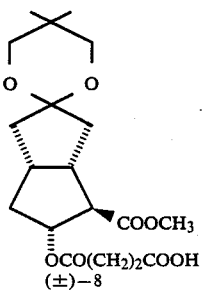

COOCH₃
OCO(CH₂)₂COOH
(±)-8

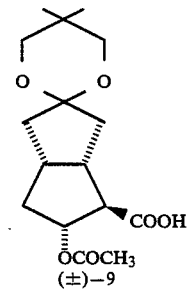

COOH
OCOCH₃
(±)-9

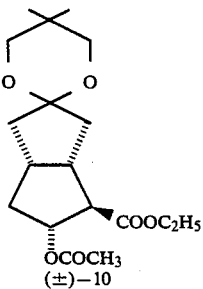

COOC₂H₅
OCOCH₃
(±)-10

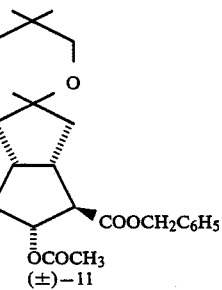

COOCH₂C₆H₅
OCOCH₃
(±)-11

Pharmacologically effective prostacyclins can be produced from the optically active 3alpha-hydroxy compounds of general formula (+)-I produced according to the process according to the invention. For example, starting from (+)-I the active ingredient Iloprost (described in EP 11591) is attained.

The strains Mucor rouxii (DSM 3897) and Alcaligenes marshallii (DSM 3900) were deposited at the German Collection of Microorganisms on 11/11/86.

Production of starting compounds:

EXAMPLE A 1

7,7-(2,2-dimethyl-trimethylenedioxy)-cis-bicyclo[3.3.-0]octan-3-one-2-carboxylic acid methyl ester 38.34 g of 55–60% sodium hydride is suspended in 616 ml of dimethyl carbonate, warmed under nitrogen to 50° C. and a small amount of solution of 49.31 g of 3,3-(2,2-dimethyltrimethylenedioxy)-cis-bicyclo[3.3.-0]octan-7-one in 370 ml of dimethyl carbonate is added. The reaction is induced by addition of 2 ml of methanol, the remaining solution is added and stirred for a total of 7.5 hours at 50° C. It is cooled in an ice bath, the excess sodium hydride is decomposed with methanol, water is added and neutralization is performed with acetic acid. The product is extracted with dichloromethane, concentrated in a vacuum and the product is crystallized with hexane. 532.44 g of product with a melting point of 72° C. is obtained.

EXAMPLE A 2

7,7-(2,2-dimethyl-trimethylenedioxy)-3alpha-hydroxy-cisbicycloi[3.3.0]octane-2beta-carboxylic acid methyl ester

Method A 52.0 g of 7,7-(dimethyl-trimethylenedioxy)-cisbicyclo[3.3.0]octan-3-one-2-carboxylic acid methyl ester is dissolved in heat in 1000 ml of methanol and cooled to −40° C. Then 20.91 g of sodium borohydride is introduced, stirred for 30 minutes, slowly mixed with 171 ml of acetone and neutralized for another hour with acetic acid. After distilling off of the main amount of the solvent, it is mixed with water and dichloromethane, the organic phase is dried with sodium sulfate and concentrated in a vacuum. The residue is taken up in 550 ml of methanol, 9.94 g of sodium methylate is added and warmed for 105 minutes to 40° C. It is cooled in an ice bath, neutralized and worked up as described above. The resulting raw product is chromatographed on silica gel with dichloromethane-ethyl acetate mixtures. 47 g of the desired compound is obtained, which can be crystallized with hexane and exhibits a melting point of 43° C.

Method B 56.6 g of 7,7-(2,2-dimehhyl-trimethylenedioxy)-cis-bicyclo[3.3.0]octan-3-one-2-carboxylic acid methyl ester is dissolved in 300 ml of ethyl acetate and is hydrogenated under normal pressure after addition of 5.1 g of platinum dioxide at 22° C. until hydrogen absorption is completed. It is filtered from the catalyst and concentrated in a vacuum. 56.8 g of the desired compound is obtained whose purity is sufficient for production of crystallizing esters. The product can be crystallized from hexane and 44.4 g of primary crystallate with a melting point of 43° C. is obtained.

EXAMPLE A3

7,7-(2,2-dimethyl-trimethylenedioxy)-3alpha-cisbicyclo[3.3.0]octane-2beta-carboxylic acid methyl ester-3-ester

(a) Acetate (±)-1

100 g of the raw product obtained according to method B in the above example is dissolved in 57 ml of pyridine and 57 ml of acetic anhydride and warmed for 3 hours to 40° C. After cooling, ice water is added, extraction with dichloromethane is performed, the organic phase is washed with 2-normal sulfuric acid, sodium bicarbonate solution and sodium chloride solution, dried with sodium sulfate, concentrated in a vacuum and the residue is crystallized from hexane. 97.6 g of product with a melting point of 54° C. is obtained.

(b) Benzoate (±)-3

5.0 g of hydroxyester raw product is dissolved in 10 ml of pyridine, mixed with 2.47 ml of benzoyl chloride and stirred for 4 hours at 22° C. Then it is slowly added in 100 ml of ice water, stirred for 30 minutes and the crystallate is suctioned off. After drying and recrystallization from methanol 5.97 g of product with a melting point 102° C. is obtained.

(c) Isobutyrate (±)-7

4.265 g of the crystallized hydroxy ester is dissolved in 40 ml of dichloromethane, mixed with 4.16 ml of triethylamine and slowly with 3.14 ml of isobutyryl chloride. After 2.5 hours 40 ml of saturated sodium bicarbonate solution at 22° C. is added, the organic phase is separated and washed with 2n sulfuric acid under ice cooling and washed with water, dried with sodium sulfate and concentrated in a vacuum. The raw product is chromatographed on silica gel with hexane-ethyl acetate mixtures. 4.91 g of product with a melting point of 43° C. is obtained.

(d) Butyrate (±)-6

4.265 g of crystallized hydroxy ester is dissolved in 10 ml of pyridine, 4.90 ml of butyric acid anhydride is added and stirred for 20 hours at 22° C. It is mixed with ice water, extracted with dichloromethane and this with sodium bicarbonate solution, under ice cooling with 2n sulfuric acid and water, dried with sodium sulfate, concentrated in a vacuum and chromatographed on silica gel with hexane-ethyl acetate mixtures. 5.03 g of product is obtained as colorless oil.

(e) Hemisuccinate (±)-8

4.265 g of crystallized hydroxy ester is dissolved in 10 ml of pyridine, 1.833 g of 4-dimethylaminopyridine and 1.501 g of succinic acid anhydride are added and stirred for 20 hours at 22° C. Then it is added to ice water, acidified with 2n sulfuric acid to pH=3, extracted with dichloromethane, washed with sodium chloride solution, dried with sodium sulfate and concentrated in a vacuum. The residue is taken up with sodium bicarbonate solution, extracted with diethyl ether, the water phase is acidified to pH =3, extracted with dichloromethane, this is washed with sodium chloride solution, dried with sodium sulfate and concentrated in a vacuum. 5.04 g of product is obtained as colorless oil.

EXAMPLE A 4

3alpha-acetoxy-7,7,-ethylenedioxy-cis-bicyclo[3.3.0]octane2beta-carboxylic acid methyl ester (+)-2

10.0 g of 7,7-ethylenedioxy-3alpha-cisbicyclo[3.3.0]octane-2beta-carboxylic acid methyl ester is reacted under the conditions of example A 3 a) and the raw product is chromatographed on silica gel with hexane-ethyl acetate mixtures. 10.28 g of product with a melting point of 50° C. is obtained.

EXAMPLE A 5

7,7-(2,2-dimethyltrimethylenedioxy)-3alpha-hydroxy-cisbicyclo[3.3.0]octane-2beta-carboxylic acid 5.0 of the crystalline hydroxy ester from example A 2 is stirred with 17.6 ml of ln sodium hydroxide solution for 30 minutes at 22° C., extracted with ethyl acetate, the aqueous phase is acidified under ice cooling with 2n sulfuric acid to pH =3, extracted with dichloromethane, washed with sodium chloride solution, dried with sodium sulfate and concentrated in a vacuum. 4.66 g of product, which is pure enough for the following reactions, is obtained.

EXAMPLE A 6

3alpha-acetoxy-7,7-(2,2-dimethyltrimethylenedioxy)-cisbicyclo[3.3.0]octane-2beta-carboxylic acid (+)-9

3.13 g of hydroxy acid from example A 5 is dissolved in 15 ml of pyridine and stirred after addition of 2.74 ml of acetic acid anhydride for 20 hours at 22° C. Ice water is added, it is stirred for 30 minutes, extracted with dichloromethane, this is washed with water, dried with sodium sulfate, concentrated in a vacuum and chromatographed on silica gel with hexane-ethyl acetate mixtures. 3.04 g of product is obtained at colorless oil.

EXAMPLE A 7

7,7-(2,2-dimethyl-trimethylenedioxy)-3alpha-hydroxy-cisbicyclo[3.3.0]octane-2beta-carboxylic acid ethyl ester 4.78 g of the hydroxy acid obtained in example A 5 is refluxed with 50 ml of acetone, 4.90 g of potassium carbonate and 5.72 ml of iodoethane for 2 days. After cooling, it is filtered, the filtrate is concentrated in a vacuum, mixed with water, extracted with dichloromethane, this is dried with sodium sulfate, concentrated and the residue is purified on silica gel with hexane-ethyl acetate mixtures. 3.65 g of product is obtained as colorless oil.

EXAMPLE A 8

3alpha-acetoxy-7,7-(2,2-dimethyltrimethylenedioxy)-cisbicyclo[3.3.0]octane-2beta-carboxylic acid ethyl ester (+) 10

3.10 g of the hydroxy ester from example A 7 is reacted under the conditions of example A 3 a) and the raw product is chromatographed on silica gel with hexane-ethyl acetate mixtures. 3.20 g of product is obtained as colorless oil.

EXAMPLE A 9

7,7-(2,2-dimethyl-trimethylenedioxy)-3alpha-hydroxy-cisbicyclo[3.3.0]octane-2beta-carboxylic acid benzyl ester 3.52 g of the hydroxy acid obtained in example A 5 is refluxed with 50 ml of acetone, 3.59 g of potassium carbonate and 3.0 ml of benzyl chloride for 5 days and worked up as described in example A 7. 2.07 g of product is obtained as colorless oil.

EXAMPLE A 10

3alpha-acetoxy-(2,2-dimethyl-trimethylenedioxy)-cis-bicyclo[3.3.0]octane-2beta-carboxylic acid benzyl ester (+)-11

1.89 g of the hydroxy ester from example A 9 is reacted under the conditions of example A 3 (a) and the raw product is chromatographed on silica gel with hexane-ethyl acetate mixtures. 1.78 g of product is obtained as colorless oil.

EXAMPLE A 11

7,7-(2,2-dimethyl-trimethylenedioxy)-cis-bicyclo[3.3.0]octan-3one-2-carboxylic acid benzyl ester 1.2 ml of benzyl alcohol and 217 ml of dimethylaminopyridine are added to a solution of 2.5 g of 7,7-(2,2-dimethyltrimethylenedioxy)-cis-bicyclo[3.3.0]octan-3-one-2-carboxylic acid methyl ester in 50 ml of toluene and the solution is refluxed for 8 hours. Then it is cooled to 25° C., saturated sodium chloride solution is added, extracted with methylene chloride, washed with brine, dried with magnesium sulfate and concentrated by evaporation in a vacuum. The residue is purified by column chromatography on silica gel. 2.6 g of the title compound is eluted with hexane/ethyl acetate 8:2 as colorless crystals. After recrystallization from ethyl acetate/hexane, 1.8 g of colorless crystals with a melting point of 78° C. is obtained.

EXAMPLE A 12

7,7-(2,2-dimethyl-trimethylenedioxy)-3alpha-hydroxy-cisbicyclo[3.3.01]octane-2beta-carboxylic acid benzyl ester 1.5 g of 7,7-(2,2-dimethyl-trimethylenedioxy)-cisbicyclo[3.3.0]octan-3-one-2-carboxylic acid benzyl ester (example 11) is dissolved in 25 ml of methanol at reflux temperature. Then it is cooled to −40° C., 470 mg of sodium borohydride is added and stirred for 1 hour at −40° C. 3.8 ml of acetone is added, stirred for 1 hour at −40° C., neutralized with about 0.7 ml of glacial acetic acid and concentrated in a vacuum. The residue is mixed with 100 ml of water, extracted with methylene chloride, washed with brine, dried with magnesium sulfate and concentrated by evaporation in a vacuum. After chromatography on silica gel with hexane/ ethyl acetate (6+4), 1.4 g of the title compound is obtained as colorless oil.

IR($CNC_3$):3600, 2960, 2870, 1722, 1447 cm$^{-1}$.

EXAMPLE A 13

7,7-(2,2-dimethyl-trimethylenedioxy)-3alpha-benzoyloxy-cisbicyclo[3.3.0]octane-2beta-carboxylic acid benzyl ester To a solution of 1.35 g of 7,7-(2,2-dimethyl-trimethylenedioxy)-3alpha-hydroxy-cis-bicyclo[3.3.0]octane2beta-carboxylic acid benzyl ester (example A 12) in 14 ml of methylene chloride are added at 0° C. 1.4 ml of pyridine and 0.62 ml of benzoyl chloride and stirred for 0.5 hour at 0° C. and 2 hours at 25° C. Then 0.2 ml of water is added, stirred for 1 hour, diluted with methylene chloride, successively shaken with water, 5% sodium bicarbonate solution and water. It is dried, over magnesium sulfate and the evaporation residue is chromatographed on silica gel. With hexane/ethyl acetate (3+2) 1.36 g of the title compound is obtained as colorless oil.

IR($CNC_3$), 2960, 2870, 1725, 1603 cm$^{-1}$

EXAMPLES

The following embodiments serve to explain the process according to the invention.

EXAMPLE 1

3 g of (±)-3alpha-acetoxy-7,7-(2,2-dimethyltrimethylenedioxy)-cis-bicyclo[3.3.0]octane-2beta-carboxylic acid methyl ester is dissolved in 100 ml of ethanol and combined with a solution of 1.5 g of lipase-PL from Alcaligenes (Meito Sangyo company) in 1 liter of 0.1M phosphate buffer pH 7 in a 2liter Erlenmeyer flask. The suspension is shaken at 30° C. on a rotary shaker, and the course of the reaction is followed by analysis of continuously taken samples. After 21 hours of reaction time, 50% of the substrate used is converted. The batch is now extracted three times with methyl isobutyl ketone, the extracts are combined and concentrated to dryness in a vacuum and for separation of the unreacted ester acylate is chromatographed over a silica gel column (gradient: methylene chloride-methylene chloride/10% acetone). 1.15 g of enantiomeric pure (+)-3alpha- hydroxy-7,7-(2,2-dimethyl-trimethylenedioxy)-cis-bicyclo[3.3.0]octane-2beta-carboxylic acid methyl ester is obtained, which, after crystallization from hexane/isopropyl ether, melts at 64°–66° C. ([alpha]$_D^{20}$+26.2°, c=1.255 in $HCC_3$).

EXAMPLE 2

300 mg of (±)-3alpha-acetoxy-7,7-(2,2-dimethyl-trimethylenedioxy)-cis-bicyclo[3.3.0]octane-2beta-carboxylic acid methyl ester is suspended in 100 ml of 0.1M phosphate buffer pH 7, 750 mg of lipase My from Candida cyclindracea (Meito Sangyo company) is added and the suspension is homogenized with a Ultra-Turrax. Then the mixture is shaken at room temperature on a rotary shaker. After 30 hours of reaction time, the substrate has reacted 50%. The batch is extracted 3 times with ether, the extracts are combined and evaporated in a vacuum to dryness. The remaining residue is chromatographed by means of a solvent gradient methylene chloride-methylene chloride/5% acetone over a silica gel column to separate the unreacted starting material. 105 mg of (+)-3alpha-hydroxy-7,7-(2,2-dimethyltrimethylenedioxy)-cis-bicyclo[3.3.0]octane-2beta-carboxylic acid methyl ester, which after crystallization from hexane exhibits a melting point of 62°–63° C. and an amount of rotation of [alpha]$_D^{20}$+25° (c=1.01 in $HCCl_3$). By comparison measurement with an authentic comparison standard an enantiomer excess of 93.6% was determined for this purpose.

EXAMPLE 3

300 mg of (±)-3-alpha-acetoxy-7,7-(2,2-dimethyl-trimethylenedioxy)-cis-bicyclo[3.3.0]octane-2beta-carboxylic acid methyl ester is dissolved in ethanol and added to a suspension of 750 mg of lipase "Saiken" from Rhizopus (Nagase company) in 100 ml of 0.1M of phosphate buffer pH 7. After 96 hours of shaking on a shaking machine at 28° C. the batch is extracted with methyl isobutyl ketone, the extract is evaporated to dryness and chromatographed over a silica gel column. 112 mg of (+)- 3alpha-hydroxy-7,7-(2,2-dimethyl-trimethylenedioxy)-cisbicyclo[3.3.0]octane-2beta-carboxylic acid methyl ester is obtained with a melting point of 64°–65° C. after crystallization from hexane. The amount of rotation is $[alpha]_D^{20} + 23.8°$ (c=1.02 in HCCl$_3$), the enantiomer excess according to comparison measurement against an authentic standard is 92.5% ee.

EXAMPLE 4

300 mg of (±)-3-acetoxy-7,7-(2,2-dimethyltrimethylenediosy)-cis-bicyclo[3.3.0]octane-2beta-carboxylic acid methyl ester is suspended in 100 ml of 0.1M phosphate buffer pH 7. 750 mg of alpha-chymotrypsin from cattle pancreas (Chemical Dynamics Corporation) is added and homogenized with the Ultra-Turrax. Then the reaction mixture is shaken at 28° C. on a rotary shaker, until the ester acylate substrate used is reacted 50%. Then the batch is extracted several times with methyl isobutyl ketone, the combined extracts are evaporated in vacuum to dryness and chromatographed by means of a solvent gradient of methylene chloride-methylene chloride/5% acetone over a silica gel column for separation of the unnaturally configured, in this case saponified, enantiomer. Fraction 1 contains the unsaponified remaining enantiomer (+)-II corresponding in its absolute configuration to natural prostacyclin PGI$_2$. After concentration to dryness, 115 mg of (+)-3alpha-acetoxy-7,7-(2,2-dimethyl- trimethylenedioxy)-cis-bicyclo[3.3.0]octahe-2beta-carboxylic acid methyl ester is obtained as uncrystallizing oil with an amount of rotation of $[alpha]_D + 2.6°$ (c=1.035 in chloroform).

EXAMPLE 5

Under the conditions of example 4, 300 mg of (±)-3alpha-acetoxy-7,7-ethlylenedioxy-cis-bicyclo[3.3.-0]octane-2-betacarboxylic acid methyl ester in phosphate buffer ph 7 is reacted with 750 mg of subtilisin from Bacillus subtilis (Boehringer Mannheim company). After 10-hours shaking at 28° C., the batch is extracted with methyl isobutyl ketone, the extract is concentrated to dryness and chromatographed over a silica gel column. Unsaponified (+) configured enantiomer, corresponding to the natural prostacyclin, is eluted as first fraction by means of the solvent gradient methylene chloride-methylene chloride /4% acetone. After concentration of the fraction to dryness, 130 mg of (+)-3alpha-acetoxy- 7,7-ethylenedioxy-cisbicyclo[3.3.-0]octane-2beta-carboxylic acid methyl ester is obtained as an oily liquid with an amount of rotation of $[alpha]_D + 2.4°$ (c=1.085 in chloroform).

EXAMPLE 6

A 2-liter Erlenmeyer flask, which contains 500 ml of a nutrient solution of 0.1% peptone, 0.2% corn steep liquor, 0.5% glucose and 0.5% yeast extract, sterilized for 30 minutes at 120° C. in an autoclave, pH adjusted to 7.5, is inoculated with a slant tube culture of the strain Alcaligenes marshallii ATCC 21030 and is shaken for 48 hours on a rotary shaker. With 300 ml of this growth culture a 10-liter fermenter is inoculated which is filled with 5 liters of a sterilized nutrient medium of the same composition as the growth culture. With the addition of silicone SH as antifoam agent it is germinated at 29° C. with aeration (5 l/min) and stirring (220 rpm). After a growth phase of 36 hours the substrate is added in the form of a sterilely filtered solution of 30 g of (±)-3alpha-acetoxy-7,7-(2,2-dimethyl-trimethylenedioxy)-cis-bicyclo[3.3.0]octane-2betacarboxylic acid methyl ester in 125 ml of ethanol and the course of the reaction is followed by analysis of continuously taken samples. Ten hours after addition of the substrate, 50% of the substrate used is reacted. The contents of the fermenter are now extracted 4 times with 3 liters each of methyl isobutyl ketone, the extracts are combined and evaporated in a vacuum to dryness. The remaining residue is dissolved in methanol and filtered through a plaited filter to remove the silicone oil. The filtrate is again brought to dryness in a vacuum and to remove the unreacted unnaturally configured (−)-II enantiomer (fraction 1) is chromatographed over a silica gel column (gradient: methylene chloride-methylene chloride/20% acetone). 10.7 g of (+)-3alpha-hydroxy-7,7-(2,2-dimethyl-trimethylenedioxy)-cisbicyclo[3.3.0]octane-2beta-carboxylic acid methyl ester is obtained in fraction 2 after crystallization from hexane with a melting point of 63°–64° C., which corresponds a enantiomer yield of 81.9% of theory. The amount of rotation is $[alpha]_D + 26.1°$ (c=1.3 in chloroform), the enantiomer excess amounts to 97.5% ee.

EXAMPLE 7

A 2-liter Erlenmeyer flask, which contains 500 ml of a nutrient solution of 3% glucose, 1.0% corn steep liquor, 0.2 NaNO$_3$, 0.1% KH$_2$PO$_4$, 0.2% K$_2$HPO, 0.05% MgSO$_4$.7H$_2$O, 0.002% FeSO$_4$.7 H$_2$O and 0.05% KCl, sterilized for 30 minutes at 120° C. in an autoclave, is inoculated with a slant tube culture of the strain Mucor rouxii (ATCC 8097) and is shaken for 2½ days to 30° C. on a rotary shaker.

With the content of two of these growth cultures a 20-liter fermenter is inoculated, which is filled with 14 liters of a medium of the same composition as the growth culture sterilized for 60 minutes at 121° C. and 1.1 bars of excess pressure. With the addition of silicone SH as antifoam agent it is germinated at 29° C. with 0.7 bar of excess pressure under aeration (15 l/min) and stirring (220 rpm). After a growth phase of 15 hours the substrate is added in the form of a sterilely filtered solution of 9 g of (±)-3alpha-acetoxy-7,7-(2,2-dimethyl-trimethylenedioxy)-cis-bicyclo[3.3.0]octane-2beta-carboxylic acid methyl ester in 220 ml of ethanol and the course of the reaction is followed by analysis of continuously taken samples.

Two hours after addition of the substrate, 50% of the substrate used is reacted. The contents of the fermenter are now extracted 3 times with 10 liters each of methyl isobutyl ketone, the extracts are combined and evaporated in a vacuum to dryness. The remaining residue is dissolved in methanol and filtered through a plaited filter to remove the silicone oil. The filtrate is again brought to dryness in a vacuum and to remove the unreacted starting material the residue is chromatographed over a silica gel column (gradient: 5 liters of methylene chloride- 5 liters of methylene chloride/10% acetone). 3.3 g of (+)-3alpha-hydroxy-7,7-(2,2-dimethyl-trimethylenedioxy)-cisbicyclo[3.3.0]octane-2beta-carboxylic acid methyl ester is obtained, which after crystallization from hexane/isopropyl ether melts at 64°–65° C. The amount of rotation is $[alpha]_D^{20} + 25.7°$ (c=1.045 in HCCl$_3$). By comparison measurement against an authentic standard the enantiomer excess was determined to be 96%.

EXAMPLE 8

A 2-liter Erlenmeyer flask, filled with 500 ml of a sterile nutrient solution of 0.1% peptone, 0.2% corn steep liquor, 0.5% glucose and 0.5% yeast extract, pH 7.3, is inoculated with a slant agar culture of the strain Corynebacterium equii (ATCC 21107) and is shaken for 48 hours at 30° C. With the content of two growth cultures a 20-liter fermenter is inoculated which is charged with 14 liters of a sterile nutrient medium of the same composition as the growth culture. With the addition of silicone SH as antifoam agent it is germinated at 29° C. and 0.7 bar of excess pressure under aeration (15 1/min) and stirring (220 rpm). After a growth phase of 16 hours the substrate is added in the form of a sterilely filtered solution of 6 g of ($\pm$)3alpha-acetoxy-7,7-(2,2-dimethyl-trimethylenedioxy)-cisbicyclo[3.3.0]octane-2beta-carboxylic acid methyl ester in 150 ml of ethanol and is again stirred an aerated. Three hours after addition of the substrate, 50% of the substrate used is converted. The batch is now extracted with methyl isobutyl ketone and the extract is concentrated in a vacuum to dryness. The remaining residue is freed of the silicone oil by methanol treatment and is chromatographed over a silica gel column. 1.9 g of (+)-3alpha-hydroxy-7,7-(2,2-dimethyl-trimethylenedioxy)-cisbicyclo[3.3.0]octane-2beta-carboxylic acid methyl ester is obtained which after crystallization from hexane/isopropyl ether melts at 63°–65° C. The amount of rotation is [alpha]$_D^{20}$+25.2° (c=1.04 in HCCCl$_3$).

EXAMPLE 9

Under the conditions of example 7, 6 g of ($\pm$)-3alpha-acetoxy-7,7-(2,2-dimethyl-trimethylenedioxy)-cisbicyclo[3.3.0]octane-2beta-carboxylic acid methyl ester is reacted with a culture of the strain of Trichoderma koningi (CBS 85068) after a fermentation time of 28.5 hours to 2.0 g of (+)-3-alpha-hydroxy-7,7-(2,2-dimethyl-trimethylenedioxy)-cisbicyclo[3.3.0]octane-2beta-carboxylic acid methyl ester. The amount of rotation of the substance crystallized from hexane is [alpha]$_D^{20}$24.2° (c=1.015 in HCCl$_3$).

EXAMPLE 10

Under the conditions of example 8, 6 g of ($\pm$)-3alpha-acetoxy-7,7-(2,2-dimethyl-trimethylenedioxy)-cisbicyclo[3.3.0]octane-2beta-carboxylic acid methyl ester is reacted with a culture of the strain of Sarcina lutea (ATCC 9341) after 135 hours of fermentation time to 1.85 g of (+)-3-alpha-hydroxy-7,7-(2,2-dimethyl-trimethylenedioxy)-cisbicyclo[3.3.0]octane-2beta-carboxylic acid methyl ester. The amount of rotation is [alpha$_D^{20}$+23.6° (c=1.010 in HCCCl$_3$).

EXAMPLE 11

Under the conditions of example 7, 6 g of ($\pm$)-3alpha-acetoxy-7,7-(2,2-dimethyl-trimethylenedioxy)-cisbicyclo[3.3.0]octane-2beta-carboxylic acid methyl ester is reacted with a culture of the strain of Penicillium citrinum (ATCC 8506) in 8 hours of fermentation time to 2.3 g of (+)-3-alpha-hydroxy-7,7-(2,2-dimethyl-trimethylenedioxy)-cisbicyclo[3.3.0]octane-2beta-carboxylic acid methyl ester. The amount of rotation is [alpha]$_D^{20}$+21.8° (c=1.05 in HCCl$_3$).

EXAMPLE 12

Under the conditions of example 8, 6 g of ($\pm$)-3alpha-acetoxy-7,7-(2,2-dimethyl-trimethylenedioxy)-cisbicyclo[3.3.0]octane-2beta-carboxylic acid methyl ester is reacted with a culture of the strain of Flavobacterium lutescens (IFO 3085) in 47 hours of fermentation time to 1.8 g of (+)-3-alpha-hydroxy-7,7-(2,2-dimethyl-trimethylenedioxy)-cisbicyclo[3.3.0]octane-2beta-carboxylic acid methyl ester. The amount of rotation is [alpha]$_D^{20}$+21.8° (c=1.145 in HCCl$_3$).

EXAMPLE 13

300 mg of ($\pm$)-3alpha-butyryloxy-7,7-(2,2-dimethyl-trimethylenedioxy)-cis-bicyclo[3.3.0]octane-2beta-carboxylic acid methyl ester is dissolved in 9 ml of ethanol and combined with a solution of 750 mg of Lipase "Saiken" from Rhizopus (Nagase company) in 100 ml of 0.1M of phosphate buffer pH 7. The suspension is shaken 150 hours at 28° C. on a rotary shaker and then extracted with methyl isobutyl ketone. The extract is concentrated in a vacuum to dryness and the residue is chromatographed over a silica gel column to separate the unreacted ester acylate. 95 mg of (+)-3alpha-hydroxy-7,7-(2,2-dimethyl-trimethylenedioxy)-cis-bicyclo[3.3.0]octane-2betacarboxylic acid methyl ester with an amount of rotation of [alpha]$_D^{20}$+22.8° (c=0.905 in HCC$_3$) is obtained.

EXAMPLE 14

Under the conditions of example 13, 300 mg of ($\pm$)-3alpha-butyryloxy-7,7-(2,2-dimethyl-trimethylenedioxy)-cisbicyclo[3.3.0]octane-2beta-carboxylic acid methyl ester in a phosphate buffer pH 7 is reacted in the presence of 750 mg of Alcalase T (Novo Industrias company). After 2.5-hours shaking at 28° C., the batch is extracted with methyl isobutyl ketone and the extract chromatographed on silica gel. 100 mg of (−)-3alpha-hydroxy-7,7-(2,2-dimethyl-trimethylenedioxy)-cisbicyclo[3.3.0]octane-2beta-carboxylic acid methyl ester with an amount of rotation of [alpha]$_D^{20}$-24.9° (c=1.020 in HCC$^3$).

EXAMPLE 15

300 mg of ($\pm$)-3alpha-dimethylacetoxy-7,7-(2,2-dimethyl- trimethylenedioxy)-cis-bicyclo[3.3.0]octane-2beta-carboxylic acid methyl ester is dissolved in 9 ml of ethanol and combined with a solution of 1.5 ml of 1:40 diluted esterase from hog liver (Boehringer company) in 100 ml of 0.1M of phosphate buffer pH 7. The mixture is shaken for 1 hour at 28° C. on the shaking machine, then extracted with methyl isobutyl ketone and the extract evaporated in a vacuum is chromatographed over a silica gel column. 114 mg of (+)-3alpha-hydroxy-7,7-(2,2-dimethyltrimethylenedioxy)-cis-bicyclo[3.3.0]octane-2beta-carboxylic acid. methyl ester is obtained as oil, which slowly crystallizes throughout. Melting point: 64°–65°; [alpha]$_D^{20}$25.1° (c=1.010 in HCCl$_3$).

EXAMPLE 16

300 mg of ($\pm$)-3alpha-carboxypropionyloxy-7,7-(2,2-dimethyltrimethylenedioxy) cis-bicyclo[3.3.0]octane-2beta-carboxylic acid methyl ester is dissolved in 9 ml of ethanol and combined with a solution of 750 mg of lipase "Sclerotinia" (Nagase company) in 100 ml of 0.1M phosphate buffer pH 7. After 30 hours shaking on a shaking machine at 28° C. the pH of the solution is adjusted with 0.1 n NaOH to pH 9.0, then extracted with methyl isobutyl ketone and the extract is concentrated in a vacuum to dryness. 105 mg of (+)-3alpha-hydroxy-7,7-(2,2-dimethyl- trimethylenedioxy)-cis-bicyclo[3.3.0]octane-2beta-carboxylic acid methyl ester with an amount of rotation of [alpha]$_D^{20}$+24.0° (c=1.08 in HCCl$_3$) is obtained.

EXAMPLE 17

300 mg of (±)-3alpha-acetoxy-7,7-(2,2-dimethyl-trimethylenedioxy)-cis-bicyclo[3.3.0]octane-2-beta-carboxylic acid ethyl ester is dissolved in 9 ml of ethanol and combined with a solution of 750 mg of lipase from hog pancreas (Chemical Dynamics Corporation) in 100 ml of phosphate buffer pH 7. The solution is shaken at 28° C. on a rotary shaker, and the course of the reaction is followed by analysis of continuously taken samples. After 1 hour of reaction time, 50% of the substrate used has been converted. The batch is extracted 3 times with methyl isobutyl ketone, the extracts are combined and evaporated in a vacuum to dryness and is chromatographed over a silica gel column (gradient: methylene chloride-methylene chloride/10% acetone) to separate the unreacted ester acylates. 110 mg of (+)-3alpha-hydroxy-7,7-(2,2-dimethyl-trimethylenedioxy)-cisbicyclo[3.3.0]octane-2beta-carboxylic acid ethyl ester with an amount of rotation of [alpha]$_D^{20}$23.8° (c=1.215 in HCCl$_3$) is obtained.

EXAMPLE 18

Under the conditions of example 17, 300 mg of (±)-3alpha-acetoxy-7,7-(2,2-dimethyl-trimethylenedioxy)-cisbicyclo[3.3.0]octane-2beta-carboxylic acid ethyl ester is treated for 1 hour with a solution of 1.5 ml (1:40 diluted) of esterase from hog liver (Boehringer Mannheim company) in 100 ml of a phosphate buffer pH 7. After extraction with methyl isobutyl ketone and chromatography over a silica gel column, 118 mg of (+)-3alpha-hydroxy-7,7-(2,2-dimethyl-trimethylenedioxy)-cisbicyclo[3.3.0]octane-2beta-carboxylic acid ethyl ester with an amount of rotation of [alpha]$_D^{20}$+24.3° (c=1.075 in HCCl$_3$).

EXAMPLE 19

Under the conditions of example 17, 300 mg of (±)-3alpha-acetoxy-7,7-(2,2-dimethyl-trimethylenedioxy)-cisbicyclo[3.3.0]octane-2beta-carboxylic acid benzyl ester is treated for 1 hour with a solution of 750 mg of lipase PL from Alcaligenes (Mcito Sangyo company) in 100 ml of a phposphate buffer pH 7. Then the batch is extracted with methyl isobutyl ketone, the extract is concentrated to dryness and the residue is chromatographed over a silica gel column. 105 mg of (+)-3alphahydroxy-7,7-(2,2-dimethyl-trimethylenedioxy)-cis-bicyclo[ 3.3.0]octane-2beta-carboxylic acid benzyl ester with an amount of rotation of [alpha]$_D^{20}$+23.9° (c=1.045 in HCCl$_3$) is obtained.

EXAMPLE 20

Under the conditions of example 17, 300 mg of (±)-3alpha-acetoxy-7,7-(2,2-dimethyl-trimethylenedioxy)-cisbicyclo[3.3.0]octane-2beta-carboxylic acid benzyl ester is treated for 3 hours with a solution of 750 mg of lipase My from Candida cylindracea (Meito Sangyo company) in 100 ml of a phosphate buffer pH 7. Then the batch is extracted with methyl isobutyl ketone, the extract is concentrated to dryness and the residue is chromatographed over a silica gel column. 115 mg of (+)-3alpha-hydroxy-7,7-(2,2-dimethyl-trimethylenedioxy)-cisbicyclo[3.3.0]octane-2beta-carboxylic acid benzyl ester with an amount of rotation of [alpha]$_D^{20}$+24.5° (c=1.145 in HCC$_3$).

EXAMPLE 21

Under the conditions of example 8, 6 g of (±)-3alpha-acetoxy-7,7-(2,2-dimethyl-trimethylenedioxy)-cisbicyclo[3.3.0]octane-2beta-carboxylic acid methyl ester is reacted with a culture of the strain Alcaligenes paradoxus (ATCC 17713). Four hours after addition of the substrate, 50% of the used racemate is converted. The batch is extracted with methyl isobutyl ketone and the extract is concentrated to dryness in a vacuum. The remaining residue is chromatographed over a silica gel column to separate the unnaturally configured saponified enantiomer. As a result the unsaponified remaining enantiomer (+)-II, corresponding in its absolute configuration to natural prostacyclin PGI$_2$, appears in fraction 1. Then the fraction is concentrated to dryness, 2.4 g of (+)-3alpha-acetoxy-7,7-(2,2-dimethyl-trimethylenedioxy)-cis-bicyclo[3.3.0]octane-2-betacarboxylic acid methyl ester is obtained as uncrystallized oil with an amount of rotation of [alpha]$_D^{20}$+2.2° (c=1.11 in chloroform).

We claim:

1. Process for the production of optically active (+)-bicyclo[3.3.0]octanol of formula (+)- I,

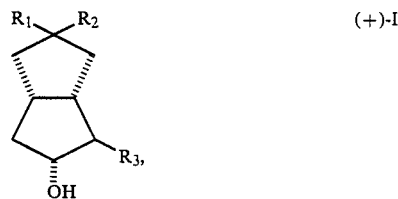

in which R$_1$ and R$_2$ together mean an oxygen atom or the double-bond radical —O—X—O— with X as straight-chain or branched-chain alkylene with 1-7 C atoms or R$_1$ and R$_2$ mean in each case the radical OR$_5$ with R$_5$ as straight-chain or branched-chain alkyl with 1-7 atoms and R$_3$ means the radical COOZ with Z as hydrogen atom, straight-chain or branched-chain alkyl with 1-7 C atoms, cycloalkyl with 3-6 C atoms, phenyl or aralkyl with 7-10 C atoms or R$_3$ means the radical —(CH$_2$)$_n$—O—COR$_4$ with n meaning 1-4 and R$_4$ as straight-chain or branched-chain alkyl with 1-7 C atoms, cycloalkyl with 3-6 C atoms, phenyl or aralkyl with 7-10 C atoms, characterized in that racemic 3alpha-acyloxy-cis- bicyclo[3.3.0]octane derivatives of the formula (±)-II,

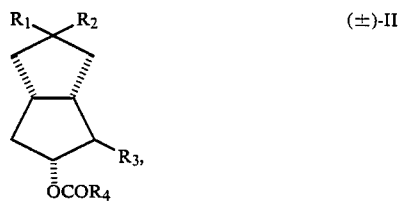

in which R$_1$, R$_2$, R$_3$ and R$_4$ have the above-indicated meanings, are enzymatically or microbiologically subjected to a stereospecific acylate hydrolysis and the resulting (+)-bicyclo[3.3.0]octanol derivative (+)-I is separated from the unsaponified bicyclo[3.3.0]octanol acylate of formula (−)-II or the unsaponified enantiomer (+)-II is separated from the saponified bicyclo[3.3.-0]octanol derivative (−)-I and then subjected to a chemical acylate hydrolysis.

2. Process according to claim 1, wherein lipase-PL from Alcaligenes, lipase My from *Candida cylindracea*, lipase Saiken from Rhizopus, lipase Sclerotinia, alpha-chymotrypsin from cattle pancreas, alcalase T, esterase from hog liver, lipase from hog pancreas, subtilisin from *Bacillus subtilis* in dissolved, suspended form or immobilized form on BrCn-activated sepharose or on oxirane acrylic beads are used as enzymes.

3. Process according to claim 1, wherein *Alcaligenes marshallii, Mucor rouxii, Corynebacterium equi, Trichoderma koningi, Sarcina lutea, Penicillium citrinum, Flavobacterium lutescens* or *Alcaligenes paradoxus* are used as microorganisms.

4. Process according to claim 3, wherein the enzymes, isolated from the microorganisms named in claim 3, are used as enzymes in dissolved, suspended or immobilized form.

5. A process for the production of optically active (+)-bicyclo[3.3.0]octanol of formula (+)-I,

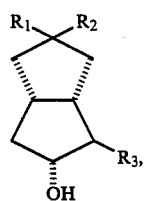

(+)-I in which $R_1$ and $R_2$ together means an oxygen atom or the double-bond radical —O—X—O— with X as straight-chain or branched-chain alkylene with 1-7 C atoms or $R_1$ and $R_2$ mean in each case the radical $OR_5$ with $R_5$ as straight-chain or branched-chain alkyl with 1-7 C atoms and $R_3$ means the radical COOZ with Z as hydrogen atom, straight-chain or branched-chain alkyl with 1-7 C atoms, cycloalkyl with 3-6 C atoms, phenyl or aralkyl with 7-10 C atoms or $R_3$ means the radical —(CH$_2$)$_n$—O—COR$_4$ with n meaning 1-4 and $R_4$ as straight-chain or branched-chain alkyl with 1-7 C atoms, cycloalkyl with 3-6 C atoms, phenyl or aralkyl with 7-10 C atoms, comprising subjecting racemic 3alpha-acyloxy-cis-bicyclo[3.3.0]octane derivatives of the formula (±)-II,

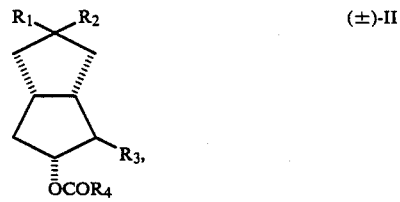

(±)-II in which Rhd 1, $R_2$, $R_3$ and $R_4$ have the above-indica enzymatic or microbiological stereospecific acylate hydrolysis.

6. A process of claim 5, wherein the products of the stereospecific acylate hydrolysis are a (+)-bicyclo[3.3.0]-octanol derivative (+)-I and an unsaponified bicyclo-[3.3.0]octanol acylate of formula (−)-II.

7. A process of claim 6, further comprising separating the resulting (+)-bicyclo[3.3.0]octanol derivative (+)-I from the unsaponified bicyclo[3.3.0]octanol acylate of formula (−)-II.

8. A process of claim 5, wherein the products of the stereospecific acylate hydrolysis are an unsaponified enantiomer (+)-II and a saponified bicyclo[3.3.0]octanol derivative (−)-I.

9. A process of claim 8, further comprising separating the resulting unsaponified enantiomer (+)-II from the saponified bicyclo[3.3.0]octanol derivative (−)-I.

10. A process of claim 9, further comprising subjecting the unsaponified enantiomer (+)-II to a chemical acylate hydrolysis.

* * * * *

UNITED STATES PATENT AND TRADEMARK OFFICE
CERTIFICATE OF CORRECTION

PATENT NO. : 4,894,336

DATED : January 16, 1990

INVENTOR(S) : KARL PETZOLDT ET AL

It is certified that error appears in the above-identified patent and that said Letters Patent is hereby corrected as shown below:

Column 16, claim 1, line 44:

reads "1-7 atoms and $R_3$ means the radical COOZ with Z as"
should read --1-7 C atoms and $R_3$ means the radical COOZ with Z as --

Column 17, claim 2, line 10:

reads "lized form on BrCn-activated sepharose or on oxirane"
should read -- lized form on CNBr-activated sepharose or on oxirane --

Column 18, claim 5, line 19:

reads "in which Rhd 1,$R_2$, $R_3$ and $R_4$ have the above-"
should read -- in which $R_1$, $R_2$, $R_3$ and $R_4$ have the above- --

UNITED STATES PATENT AND TRADEMARK OFFICE
CERTIFICATE OF CORRECTION

PATENT NO. : 4,894,336

DATED : January 16, 1990

INVENTOR(S) : KARL PETZOLDT ET AL

Page 2 of 2

It is certified that error appears in the above-identified patent and that said Letters Patent is hereby corrected as shown below:

Column 18, claim 5, line 20:

reads "indica enzymatic or microbiological stereospecific"

should read indicated meanings, to enzymatic or microbiological stereospecific--

Signed and Sealed this

Second Day of July, 1991

Attest:

HARRY F. MANBECK, JR.

Attesting Officer

Commissioner of Patents and Trademarks